US012734115B2

(12) United States Patent
Ueda et al.

(10) Patent No.: US 12,734,115 B2
(45) Date of Patent: Sep. 15, 2026

(54) COSMETIC LAMINATE SHEET

(71) Applicant: PANASONIC INTELLECTUAL PROPERTY MANAGEMENT CO., LTD., Osaka (JP)

(72) Inventors: Mari Ueda, Osaka (JP); Masato Minami, Hyogo (JP); Yuto Enomoto, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 377 days.

(21) Appl. No.: 18/126,186

(22) Filed: Mar. 24, 2023

(65) Prior Publication Data

US 2023/0255859 A1 Aug. 17, 2023

Related U.S. Application Data

(63) Continuation of application No. PCT/JP2021/043026, filed on Nov. 24, 2021.

(30) Foreign Application Priority Data

Dec. 18, 2020 (JP) ................................ 2020-210120

(51) Int. Cl.
*A61K 8/02* (2006.01)
*A61K 8/73* (2006.01)
*A61Q 19/00* (2006.01)

(52) U.S. Cl.
CPC ............ *A61K 8/0212* (2013.01); *A61K 8/731* (2013.01); *A61Q 19/007* (2013.01)

(58) Field of Classification Search
CPC ............ A61K 8/0212; B32B 2307/726; B32B 2307/728; B32B 3/266; B32B 2307/7376
See application file for complete search history.

(56) References Cited

U.S. PATENT DOCUMENTS

| | | | | |
|---|---|---|---|---|
| 9,585,461 | B2 * | 3/2017 | Kusukame | A45D 44/002 |
| 10,544,319 | B2 * | 1/2020 | Kusukame | C09D 11/36 |
| 2015/0004391 | A1 * | 1/2015 | Nair | C08J 9/28 521/84.1 |
| 2015/0265030 | A1 * | 9/2015 | Kusukame | A45D 44/002 132/320 |
| 2021/0060898 | A1 | 3/2021 | Morishima et al. | |
| 2021/0228457 | A1 | 7/2021 | Ishida et al. | |

FOREIGN PATENT DOCUMENTS

| | | |
|---|---|---|
| CN | 105200656 | 12/2015 |
| CN | 111885992 | 11/2020 |
| EP | 3 928 658 | 12/2021 |
| EP | 3 949 801 | 2/2022 |
| JP | 2003-135146 | 5/2003 |
| JP | 2015-193604 | 11/2015 |
| JP | 2018-177804 | 11/2018 |
| JP | 2019-142238 | 8/2019 |
| WO | 2019/220936 | 11/2019 |
| WO | 2020/170633 | 8/2020 |

OTHER PUBLICATIONS

Chitrattha et al (Materials Science and Engineering: C, Jan. 2016, vol. 58, pp. 1122-1130) (Year: 2016).*
International Search Report issued in International Patent Application No. PCT/JP2021/043026, dated Feb. 1, 2022.
Extended European Search Report issued in EP Application No. 21906281.7, dated Mar. 1, 2024.

* cited by examiner

*Primary Examiner* — Mark V Stevens
(74) *Attorney, Agent, or Firm* — GREENBLUM & BERNSTEIN, P.L.C.

(57) ABSTRACT

An aspect of the present invention relates to a cosmetic laminate sheet including a thin film sheet that has a thickness of 10 nm or more and 10 μm or less and is water-permeable and a support that has water absorbing properties and a possible amount of water content in the support being 4.4 g or more per 1 g of the support.

9 Claims, 3 Drawing Sheets

COSMETIC LAMINATE SHEET

TECHNICAL FIELD

The present invention relates to a cosmetic laminate sheet.

BACKGROUND ART

For cosmetic purposes, it is a well-known cosmetic method to simply pack the face with a face mask in which a sheet-like substrate is impregnated with cosmetic ingredients. For example, Patent Literature 1 discloses a face mask in which a liquid impregnated substrate containing a cosmetic liquid and a liquid blocking film are superimposed one on another.

In recent years, it has also been reported that sheets formed of nanofibers are applied to the medical fields and the fields of cosmetics. For example, Patent Literature 2 discloses a method for forming a film on the skin surface using a nanofiber sheet, which includes (1) a step (1) of applying a sheet clarifying agent containing one or two or more oils at 2% by mass or more to the skin; and (2) a step (2) of transferring a white nanofiber sheet containing a water-insoluble polymer as a main ingredient to the skin after subjected to the step (1), as a method for forming a transparent film that comes into highly close contact with the skin and allows the skin to be visually recognized.

Patent Literature 3 discloses a fibroin nano thin film, which contains fibroin and has a contact angle with water of 30° or more, as a fibroin nano thin film exhibiting excellent attaching properties.

In a face mask as described in Patent Literature 1 above, a nonwoven fabric or the like as a substrate is impregnated with cosmetic ingredients and attached to the face. However, such conventional face masks can only be worn for about 5 to 15 minutes, and have disadvantages that the nonwoven fabric absorbs moisture from the skin and evaporates moisture from the surface as the nonwoven fabric dries, so the original moisture of the skin is also taken when the face mask is worn for a long time.

The face mask has a shape that covers the entire face, and thus has an unnatural appearance. In addition, since the face mask may come off due to its weight as the user moves while wearing the face mask, movement is restricted while the user wears the face mask. Furthermore, since the face mask is a type that is attached to the entire face, the permeation of cosmetic ingredients is inevitably wide and shallow, and for example, it is difficult for the cosmetic ingredients to permeate around the eyes, mouth and the like locally and intensively.

Meanwhile, since the thin film nanosheets described in Patent Literatures 2 and 3 are extremely thin, it is difficult to attach the sheet to the skin without causing wrinkling or the like. Therefore, there is a problem that the attaching operation is complicated and the user cannot attach the nanosheet to the skin well. For example, in Patent Literature 3, the thin film is attached after the skin surface is moistened with makeup or the like, but it is known that the nanosheet is likely to be twisted by moisture and cannot be attached well by such a method.

The present invention is made in view of such circumstances, and a main object thereof is to provide a cosmetic laminate sheet, which can be used for a long time and locally and intensively, does not interfere with activities while being worn, and can be attached to an adherend by a relatively easy operation by a user.

CITATION LIST

Patent Literatures

Patent Literature 1: JP 2003-135146 A
Patent Literature 2: JP 2018-177804 A
Patent Literature 3: JP 2019-142238 A

SUMMARY OF INVENTION

As a result of intensive studies, the present inventors found out that the problems can be solved by a cosmetic laminate sheet having the following configuration, and completed the present invention by conducting further studies based on this finding.

In other words, the cosmetic laminate sheet related to an aspect of the present invention includes a thin film sheet that has a thickness of 10 nm or more and 10 μm or less and is water-permeable, and a support that is laminated on the thin film sheet and has water absorbing properties, and a possible amount of water content in the support is 4.4 g or more per 1 g of the support.

DESCRIPTION OF EMBODIMENTS

Figure 1A:
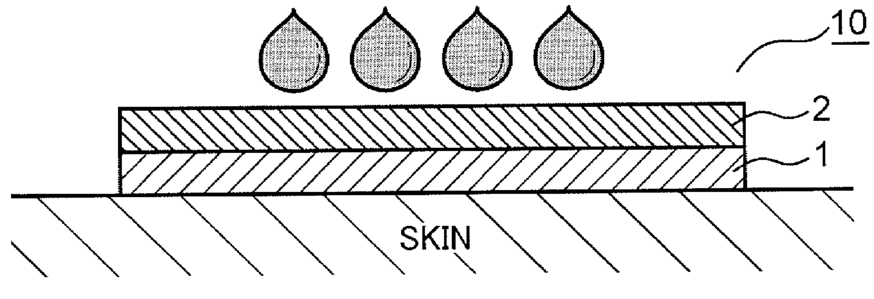
FIGS. 1A, 1B, and 1C are schematic sectional views illustrating an example of a method for attaching a cosmetic laminate sheet according to an embodiment of the present invention.

Hereinafter, embodiments according to the present invention will be specifically described, but the present invention is not limited thereto.

(Cosmetic Laminate Sheet)

As described above, the cosmetic laminate sheet of the present embodiment includes a thin film sheet that has a thickness of 10 nm or more and 10 μm or less and is water-permeable and a support that is laminated on the thin film sheet and has water absorbing properties, and the possible amount of water content in the support is 4.4 g or more per 1 g of the support. Alternatively, the possible amount of water content in the support is 10 $mg/cm^2$ or more and 17 $mg/cm^2$ or less when calculated in terms of the area of the support.

As the cosmetic laminate sheet is equipped with a support, which has water absorbing properties and has a possible amount of water content within the above range, in this way, the cosmetic ingredients can permeate into desired places for a longer time than those of conventional face masks. Since the thin film sheet of the present embodiment has a thickness of 10 nm or more and 10 μm or less, uncomfortable feeling is not caused and there is no fear that the sheet comes off by its own weight when the sheet is attached to the skin or the like. Therefore, there is an advantage that activities are not particularly restricted while the sheet is attached, and daily activities can be performed while the sheet is attached.

Therefore, according to the present invention, it is possible to provide a cosmetic laminate sheet, which can be used for a long time and locally and intensively, does not interfere with activities while being worn, and can be attached to an adherend by a relatively easy operation by a user.

The cosmetic laminate sheet (hereinafter also simply referred to as "laminate sheet") of the present embodiment includes at least a thin film sheet and a support.

The cosmetic laminate sheet of the present embodiment may be a single sheet, or can be a tear-off patch type sheet having a desired size and perforations.

Each component of the laminate sheet of the present embodiment will be described in more detail.

(Thin Film Sheet)

The thin film sheet equipped in the cosmetic laminate sheet of the present embodiment is a sheet with a thickness of 10 nm or more and 10 μm or less to be stuck to the skin. When the thickness of the thin film sheet is within the above range, there is an advantage that uncomfortable feeling is not caused when the sheet is stuck to the adherend such as the skin. The thickness of the thin film sheet is still more preferably 100 nm to 1000 nm.

The thin film sheet is used for cosmetic purposes, and is thus a water-permeable thin film sheet through which cosmetic ingredients can permeate. In the present embodiment, being water-permeable means having a property of allowing water to pass through, specifically means having a fine structure through which water molecules can pass. As the thin film sheet is water-permeable, water (liquid cosmetic ingredients) can be dropped on a support to be described later, pass through the thin film sheet, and reach the skin.

The thin film sheet of the present embodiment is preferably a biocompatible sheet-like member that does not cause uncomfortable feeling when attached to human skin. Preferably, the thin film is usually colorless and transparent or translucent.

The shape of the thin film sheet in plan view is not particularly limited, and is appropriately selected according to the shape of the attachment portion of the thin film sheet and the application. The thin film sheet may have cuts formed on the outer periphery and/or in the plane so as to fit the shape of the attachment portion.

The thin film sheet may be a sheet formed by a spin coating method, a roll-to-roll method, an LB method (Langmuir-Blodgett method), or the like, a fiber sheet in which fibers generated by an electrospinning method or the like are folded, or the like.

The thin film sheet of the present embodiment preferably has pores. Thus, it is considered that the water permeability described above can be sufficiently secured. The diameter of the pores is preferably 1 nm or more and 100 μm or less. The diameter of pores refers to the average value of diameters of the micropores.

In the thin film sheet of the present embodiment, the "pores" are preferably through holes in order to enhance water permeability. The shape of the pores may be circular, elliptical, polygonal (including a honeycomb structure), a fine structure in which these are irregularly mixed, or the like, but is preferably circular from the viewpoint of workability.

When the minimum diameter of the pores is 1 nm or more, water (molecules) can sufficiently pass through the pores. As the maximum diameter of the pores is 100 μm or less, it is considered that sufficient water can be retained. In other words, as pores having a diameter as described above are equipped, the thin film sheet of the present embodiment has both a function of reliably allowing cosmetic ingredients to pass and a function of preventing evaporation of the cosmetic ingredients from the surface and thus further has the advantage of being able to retain the cosmetic ingredients for a longer time.

A more preferable range of the diameter of the pores is 1 nm or more and 10 μm or less.

The porosity of the thin film sheet (proportion of pores in the thin film sheet) of the present embodiment is 1% or more and 10% or less in area ratio.

Furthermore, in the present embodiment, the thin film sheet is preferably hydrophilic. Being hydrophilic means that the contact angle of the thin film sheet with water is 90° or less. A more preferable contact angle is 50° or less. As the thin film sheet is hydrophilic, it is considered that a water-soluble layer is likely to be formed on the surface of the thin film sheet and the cosmetic ingredients can be retained for a longer time.

The contact angle with water herein can be a value measured by the θ/2 method or by determining the angle of the straight line connecting the left and right end points and the apex of a droplet with respect to the solid surface and doubling this.

In particular, when the contact angle of water to the skin is larger than the contact angle of the thin film sheet, and the difference therebetween is about 30° to 120°, it is considered that the cosmetic ingredients can be more reliably introduced into the skin.

The material forming the thin film sheet is not particularly limited as long as it is a material having biocompatibility, but examples thereof include polyesters represented by polyglycolic acid, polylactic acid, polycaprolactone, polyethylene succinate, polyethylene terephthalate, or copolymers thereof; polyethers represented by polyethylene glycol and polypropylene glycol; polyamides represented by nylon, polyglutamic acid, polyaspartic acid, or salts thereof; polysaccharides represented by pullulan, cellulose, starch, chitin, chitosan, alginic acid, hyaluronic acid, and cornstarch, or salts thereof; silicones represented by acrylic silicones and trimethylsiloxysilicates; acrylic acids represented by alkyl acrylates, silicone acrylates, acrylic acid amides, and copolymers thereof; polyvinyl alcohol; polyurethane; polycarbonate; polyanhydrides; polyethylene; polypropylene; porous layer coating sheets, and nanofiber sheets.

Among these, it is preferable that the material for the thin film sheet is polylactic acid, cellulose (for example, carboxymethylcellulose or hydroxyethylcellulose), starch, chitin, chitosan, alginic acid, corn starch, or polyurethane since there are advantages such as biocompatibility, easy availability, and favorable handleability. From the viewpoint of biocompatibility, easy availability, and handleability, polylactic acid, cellulose (for example, carboxymethylcellulose or hydroxyethylcellulose), starch, chitin, chitosan, or polyurethane are particularly preferable among these.

Preferably, it is preferable to use materials such as polylactic acid, cellulose (for example, carboxymethylcellulose or hydroxyethylcellulose), starch, chitin, or chitosan in order to form a hydrophilic thin film sheet.

(Support)

The laminate sheet of the present embodiment has a support. The support is a plate-shaped member disposed on the surface of the thin film sheet described above, and is used to protect the thin film sheet described above and to allow the thin film sheet to retain the cosmetic ingredients.

The support used in the present embodiment has water absorbing properties. Exhibiting water absorbing properties means having a structure (for example, pores) capable of retaining water inside. In the case of a laminate sheet equipped with such a support, sufficient cosmetic ingredients can be delivered to the skin for a long time by attaching the above-described thin film sheet side to the skin and spraying cosmetic liquids for moisturizing and whitening from the support side, and allowing the cosmetic liquids to pass through.

The possible amount of water content in the support is 4.4 g or more per 1 g of the support. The upper limit is not particularly limited, but the possible amount of water content in the support is preferably 12 g or less per 1 g of the support from the viewpoint of preventing moisture from being taken from the thin film sheet and the skin. The possible amount of water content means the amount of water that can be contained, and is a value that can be measured by weighing the difference in weight of the support before and after the support contains water using an electronic balance or the like, and converting the difference in weight to a difference in weight per 1 g of the support.

Alternatively, the possible amount of water content may be a value that can be measured by dividing the difference in weight of the support before and after the support contains water by the sectional area of the support. In that case, the possible amount of water content is 10 $mg/cm^2$ or more and 17 $mg/cm^2$ or less.

As the possible amount of water content is within the above range, the support of the present embodiment can deliver an appropriate amount to the skin without repelling water or absorbing too much water when water (liquid cosmetic ingredients) is sprayed or applied onto the support.

A more preferable range of the possible amount of water content is about 10 g or more and 12 g or less per 1 g of the support.

The shape of the support is not particularly limited as long as it can cover one surface of the thin film sheet. The shape of the support in plan view may be the same as that of the thin film sheet, or may be larger than that of the thin film sheet. For example, the support may have a gripping margin or the like for gripping when the support is peeled off from the thin film sheet.

The thickness of the support is preferably 50 to 2000 μm, more preferably 100 to 1500 μm. When the thickness of the support is within the above range, there are advantages that the support is likely to be grasped with fingers, tweezers, or the like when the support is peeled off from the thin film sheet, and the support is likely to be peeled off since suitable flexibility is imparted to the support.

The support of the present embodiment is formed of a water absorbing material capable of retaining water inside. The support is preferably formed of a material that further has hydrophilicity. Being hydrophilic is synonymous with hydrophilicity described in the above-described thin film sheet.

As the material for the support, any material having the properties as described above can be used without particular limitation, but examples thereof include hydrophilic polymers, paper (cellulose), and nonwoven fabrics. More specifically, examples of hydrophilic polymers include polyolefins (for example, polyethylene, low-density polyethylene, and polypropylene), ethylene vinyl acetate resin, synthetic rubber, copolyamide resin, copolyester resin, epoxy resin, polyurethane, polysiloxane, polyvinyl alcohol, acrylic resin, polyhydroxyethyl methacrylate, and synthetic resins thereof, and examples of nonwoven fabrics include nonwoven fabrics of glass fibers, cellulose, rayon, polyester, nylon, polypropylene, acrylic fibers, vinylon, aramid fibers, and synthetic fibers thereof. In addition to the above, porous films, nanofiber sheets, and the like can also be used. From the viewpoint of hydrophilicity, easy availability, and handleability, more preferable ones among these include paper (cellulose), hydrophilic polymers such as polyolefins (polyethylene, low-density polyethylene, and polypropylene), copolyamide resin, copolyester resin, epoxy resin, polyurethane, polyvinyl alcohol, acrylic resin, and synthetic resins thereof, nonwoven fabrics such as nonwoven fabrics of cellulose, rayon, polyester, and synthetic fibers thereof, nanofiber sheets, and the like.

Among these, as a material having a possible amount of water content of 4.4 g or more per 1 g of the support, paper (cellulose), and hydrophilic polymers such as polyolefins (polyethylene, low-density polyethylene, and polypropylene), copolyamide resin, copolyester resin, epoxy resin, polyurethane, polyvinyl alcohol, acrylic resin, and synthetic resins thereof are preferably used.

As a material having a possible water content of 10 g or more per 1 g of the support, nonwoven fabrics of cellulose, rayon, polyester, synthetic fibers thereof, and the like, and nonwoven fabrics such as nanofiber sheets are preferably exemplified.

Among the materials mentioned above, it is particularly preferable to use paper (cellulose) and nonwoven fabrics. This is because these are particularly excellent in water absorbing properties (water content) and hydrophilicity. The fact that the support is excellent in hydrophilicity means that the support does not repel water (moisturizing liquid), helps the moisturizing liquid get wet and spread widely and uniformly thereon, and further has high water absorbing properties. By using a support having such properties, the cosmetic laminate sheet of the present embodiment can retain a sufficient amount of liquid (moisturizer and the like) containing cosmetic ingredients to be introduced between the thin film sheet and the skin.

The support may or may not have optical transparency. The support may be colored.

The support is preferably flexible, and the elastic modulus of the support is preferably 100 to 100000 MPa, more preferably 100 to 5000 MPa. The elastic modulus is a value measured by any of a static test method, a transverse vibration method, or an ultrasonic method. The JIS standards for elastic modulus measurement are JIS Z2280, JIS R1602, and JIS R1605, and the elastic modulus is a value measured in conformity with any of these. More specifically, the elastic modulus in the present specification can be a value measured using an elastic modulus measuring device based on a static test method (bending test), a transverse vibration method, a cantilever resonance method, or an ultrasonic method (pulse echo overlap method). When the elastic modulus of the support is within this range, breakage and the like are unlikely to occur when the support is peeled off from the thin film sheet, and the support can be appropriately deformed.

(Method for Fabricating Cosmetic Laminate Sheet)

The method for fabricating a cosmetic laminate sheet of the present embodiment is not particularly limited, but the cosmetic laminate sheet can be fabricated by preparing the thin film sheet described above and the support described above, and laminating the support so that the support faces the previously fabricated thin film sheet. Since the thin film sheet is extremely thin in the laminate sheet of the present embodiment, the support can be attached to the thin film sheet by intermolecular force by simply laminating the support, and an adhesive or the like is not required.

(Method for Attaching Cosmetic Laminate Sheet)

Next, a method for attaching the thin film sheet equipped in the cosmetic laminate sheet to an adherend will be described with reference to FIG. 1. In the following description, reference numerals in each drawing respectively denote: 1 thin film sheet, 2 support, and 10 cosmetic laminate sheet.

Figure 1B:
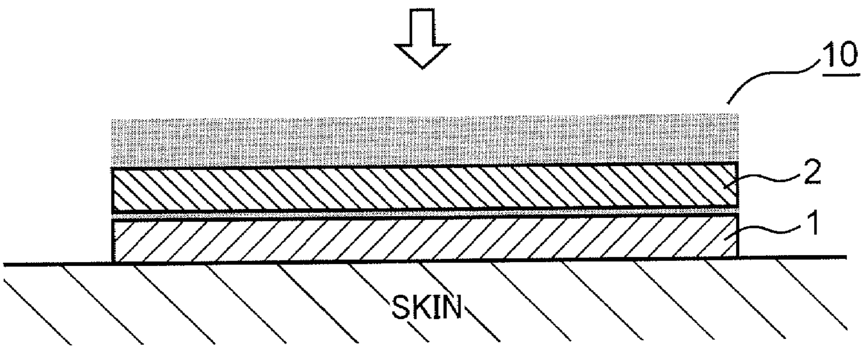
Figure 1C:
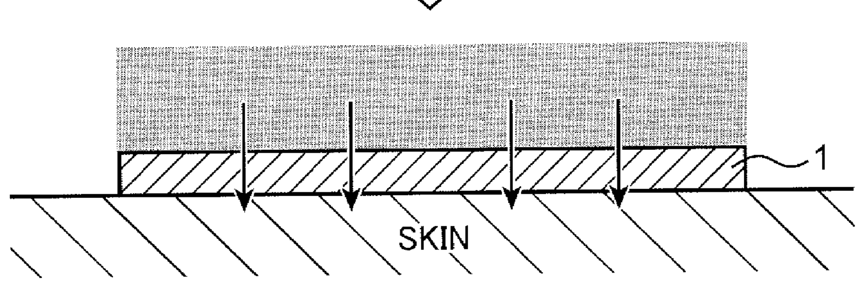

FIG. 1(A) to FIG. 1(C) are sectional views illustrating an example of the method for attaching the cosmetic laminate sheet of the present embodiment. However, the method of using the laminate sheet of the present embodiment is not limited to the following method.

First, a laminate sheet 10 in which a thin film sheet 1 and a support 2 are laminated as illustrated in FIG. 1(A) is placed on a desired adherend such that the thin film sheet 1 is in contact with the adherend (skin). Then, cosmetic ingredients (liquid) such as lotion, milky lotion, and whitening ingredients are sprayed over the entire support from the support side. The spraying method is not limited, and spraying can be performed by spraying, atomizing, direct coating, direct dropping, dropping through a mechanism such as a dropper or sponge, or the like.

Alternatively, the laminate sheet may be immersed in a container or the like containing the cosmetic ingredients (liquid) and then placed on the adherend in addition to the method in which the laminate sheet is placed on the adherend and then the cosmetic ingredients are sprayed as described above.

Since the support 2 of the present embodiment exhibits water absorbing properties and has a possible amount of water content as described above, the cosmetic ingredients permeate the support 2 and the thin film sheet 1 as illustrated in FIG. 1(B).

After that, the support 2 is peeled off from the thin film sheet 1. According to the laminate sheet 10 of the present embodiment, after the support 2 is removed as well, the cosmetic ingredients can permeate the place where the thin film sheet 1 is placed over a long time as illustrated in FIG. 1(C). Since the thin film sheet 1 of the present embodiment is extremely thin, there is an excellent advantage of not interfering with the user's activities while the sheet is worn.

There is no particular limitation on the time during which the sheet of the present embodiment can be attached to the skin and the cosmetic ingredients can permeate, and the time can be appropriately set according to the kind and amount of cosmetic ingredients, user's activities, and the like.

Cosmetic ingredients that can be used with the laminate sheet of the present embodiment are not particularly limited as long as they are liquid. As cosmetic ingredients such as moisturizing ingredients and whitening ingredients, known ingredients can be used without particular limitation.

For example, a moisturizing ingredient preferably has a function of imparting moisture and a barrier function to the stratum corneum of the skin. More preferably, a moisturizing ingredient is an ingredient that plays a role in assisting the function of sebum secreted from the skin. The moisturizing liquid (liquid containing a moisturizing ingredient) may contain a solvent for dispersing the moisturizing ingredient if necessary.

Moisturizing ingredients are preferably selected from ingredients listed in the list of cosmetic ingredient display names based on the Pharmaceutical Affairs Law of Japan, ingredients that comply with the EU Cosmetics Directive (Cosmetics Directive 76/768/EEC), ingredients listed in the International Cosmetic Ingredient Dictionary and Handbook (Jan. 1, 2002, 9th edition) by the US CTFA (Cosmetic, Toiletry & Fragrance Association, U.S.), and the like. Examples thereof include fatty acids (for example, stearic acid, linoleic acid, oleic acid, and lauric acid), fatty alcohols, cholesterol, squalene, palm oil, coconut oil, urea, lactic acid, glycerin, propylene glycol, hyaluronic acid, alpha hydroxy acid (AHA), honey, mineral oil, petroleum raw materials, petroleum jelly, beeswax, silicone, zinc oxide, lecithin, vegetable oils (for example, olive oil, sunflower oil, grape seed oil, coconut oil, safflower seed oil, argan oil, soybean oil, peanut oil, sesame oil, avocado oil, borage oil, jojoba oil, oat oil, pomegranate seed oil, almond oil, bitter apricot oil, rosehip oil, German chamomile oil, and shea butter), L-oxyproline, L-lysine liquid, asparagus stem extract, althaea extract, apricot seed extract, dog rose extract, lysine hydrochloride, hydrolyzed conchiolin, hydrolyzed silk powder, kakkon extract, caninabara fruit extract, raspberry extract, kiwi extract, gourd extract, kudzu root extract, *gardenia* extract, mulberry extract, *Gentiana lutea* extract, rice bran extract, sericin, soybean extract, thyme extract, clove extract, *Rosa multiflora* fruit extract, wild rose extract, hibiscus flower extract, pearl barley seed extract, hydroxyproline, prune enzymatic decomposition product, *Morus alba* root bark extract, madonna lily root extract, marjoram extract, lily extract, *coix* seed extract, ricin, linolenic acid, and wild thyme extract. These can be used singly or in combination of two or more thereof.

Among these, fatty acids (stearic acid, linoleic acid, oleic acid, and lauric acid), fatty alcohols, cholesterol, squalene, palm oil, and coconut oil are more preferable from the viewpoint of biosafety. Examples of fatty alcohols include trihydric alcohols such as glycerin, dihydric alcohols such as diethylene glycol, propylene glycol, 1,3-propanediol, butylene glycol, and hexanediol, and monohydric alcohols such as propanol, isopropanol, and butyl alcohol.

The amount of the moisturizing ingredient in the moisturizing liquid (in the liquid containing the moisturizing ingredient) is not particularly limited, but is preferably 1% by mass or more, more preferably 1% to 100% by mass, still more preferably 1% to 50% by mass from the viewpoint of achieving both moisturizing properties and handleability (easy peeling off of the support 2 from the thin film sheet 1). When the amount of the moisturizing ingredient in the moisturizer layer increases, the thin film sheet 1 is sticky in some cases. In addition, it is difficult to peel off the support 2 from the thin film sheet 1 in some cases.

Meanwhile, the solvent may be any one as long as it does not irritate the skin, and water, ethanol, and polyhydric alcohols (1,3-butylene glycol, dipropylene glycol, propylene glycol and the like) are preferable, among these, water is more preferable. The amount of the solvent in the liquid is appropriately selected according to the desired viscosity of the liquid, but is preferably 99% by mass or less, more preferably 50% to 99% by mass.

Examples of whitening ingredients include vitamin C, vitamin E, arbutin, retinol, hyaluronic acid, collagen, pearl barley extract, seaweed extract, tranexamic acid, elastin, placenta extract, magnesium L-ascorbyl phosphate, sodium L-ascorbyl phosphate, kojic acid, L-ascorbic acid 2-glucoside, ellagic acid, 4-n-butylresorcinol, chamomile ET, linoleic acid S, 4-methoxysalicylic acid potassium salt, 3-O-ethylascorbic acid, disodium adenosine monophosphate, 5,5'-dipropyl-biphenyl-2,2'-diol, tetra 2-hexyldecanoic acid ascorbyl EX, nicotinamide, TXC, dexpanthenol W, 3-O-ethylascorbic acid, L-oxyproline, L-lysine liquid, α-arbutin, artichoke leaf extract, astaxanthin, asparagus stem extract, adenosine monophosphate disodium OT, althaea extract, *arnica* extract, apricot seed extract, disodium isostearylascorbyl phosphate, Japanese knotweed root extract, turmeric extract, *Asarum sieboldii* root extract, bearberry leaf extract, dog rose fruit extract, lysine hydrochloride, Scutellaria *baicalensis* root extract, hydrolyzed conchiolin, hydrolyzed silk powder, kakkon extract, caninabara fruit extract, caprylyl 2-glyceryl ascorbate, *Artemisia capillaris* extract, licorice root extract, licorice flavonoid, raspberry extract, kiwi extract, gourd extract, kudzu root extract, *gardenia* extract, *Sophora angustifolia* extract, mulberry extract, *Gentiana lutea* extract, rice bran extract, carambola leaf extract, Asiasari radix extract, *Lithospermum* root extract, peony extract, Acorus calamus root extract, honeysuckle extract, starfruit leaf extract, sericin, soybean extract, thyme extract, clove extract, ascorbyl tetra-2-hexyldecanoate, ascorbyl tetrahexyldecanoate, *Angelica acutiloba* extract, niacinamide, *Ruscus aculeatus* root extract, nicotinamide, *Rosa multiflora* fruit extract, wild rose extract, hydroquinone, hibiscus flower extract, pearl barley seed extract, trisodium ascorbyl palmitate phosphate, *Isodon japonicus* extract, hydroxyproline, loquat leaf extract, ferulic acid, butcher's broom extract, grape seed extract, prune enzymatic decomposition product, safflower extract, *Haematococcus pluvialis* extract, *Haematococcus pluvialis* oil, *Paeonia suffruticosa* extract, *Morus alba* root bark extract, madonna lily root extract, marjoram extract, *Lithospermum erythrorhizon* root extract, evening primrose seed extract, melissa extract, strawberry geranium extract, lily extract, *coix* seed extract, ricin, linolenic acid, rooibos extract, rosemary extract, wild thyme extract, and burnet extract. The amount of the whitening ingredient in the whitening liquid (in the liquid containing the whitening ingredient) and the solvent that may be contained in the whitening liquid include the same amounts and solvents as those of the moisturizing ingredients described above.

Furthermore, as the cosmetic ingredients of the present embodiment, for example, other ingredients such as anti-aging ingredients can also be used.

The cosmetic ingredients described above can be used singly or in combination of two or more thereof (for example, combination of a moisturizing ingredient and a whitening ingredient).

The liquid containing cosmetic ingredients may contain a surfactant and other ingredients that may be contained in the cosmetic liquid in addition to the cosmetic ingredients and solvent described above. Examples of surfactants include anionic surfactants, cationic surfactants, amphoteric surfactants, and nonionic surfactants, and surfactants are preferably selected from ingredients listed in the list of cosmetic ingredient display names based on the Pharmaceutical Affairs Law of Japan, ingredients that comply with the EU Cosmetics Directive (Cosmetics Directive 76/768/EEC), ingredients listed in the International Cosmetic Ingredient Dictionary and Handbook (Jan. 1, 2002, 9th edition) by the US CTFA (Cosmetic, Toiletry & Fragrance Association, U.S.), and the like.

The amount of other ingredients is not particularly limited as long as the objects and effects of the present disclosure are not impaired, but the amount of other ingredients in the cosmetic liquid (in the liquid containing cosmetic ingredients) is preferably 50% by mass or less, more preferably 10% by mass or less.

Although not particularly limited, the viscosity of the liquid containing cosmetic ingredients is preferably 1.1 mPa·s or more, more preferably 1.2 mPa·s or more, still more preferably 1.3 to 1500 mPa·s as the viscosity measured at a shear rate of 2000 $s^{-1}$ using a cone and plate viscometer. When the viscosity of the liquid is 1.1 mPa·s or more, the cosmetic ingredients are likely to stay on the surface of the thin film sheet 1 and the above-described effects are likely to be acquired.

The method for preparing a liquid containing cosmetic ingredients as described above is not particularly limited, and can be the same as a known method for preparing a cosmetic containing cosmetic ingredients.

Hereinafter, the present invention will be described more specifically with reference to Examples, but the scope of the present invention is not limited to these.

EXAMPLES (Fabrication of Laminate Sheet)

In the present Examples, a polylactic acid sheet having a thickness of 200 nm was used as the thin film sheet. The thin film sheet had a maximum pore diameter of 100 nm and a minimum pore diameter of 10 nm.

On the thin film sheet, a support formed of cellulose and having a shape larger than that of the thin film sheet in plan view was laminated to obtain a laminate sheet. In the lamination method, the thin film sheet and the support were each wetted with water, then the thin film sheet and the support were attached to each other and dried for 12 hours or more. The possible amount of water content in the support is 11 g per 1 g of the support (16 mg/$cm^2$ when calculated in terms of the area of the support).

Test Example 1: Confirmation of Moisturization Lasting Effect

A 3 cm square piece of the laminate sheet obtained above was attached to the skin of a subject, and then 150 mL of a commercially available moisturizing lotion as a liquid containing a moisturizing ingredient was sprayed over the support by atomizing. Then, it stood by for 10 seconds until the lotion had sufficiently permeated the entire support, and then the support was peeled off.

Then, in each of a case where the thin film sheet was peeled off wen 5 minutes elapsed since attachment, a case where the thin film sheet was peeled off when 1 hour elapsed since attachment, a case where the thin film sheet was peeled off when 2 hours elapsed since attachment, and a case where lotion was sprayed directly on the skin without using the thin film sheet (without attaching the thin film sheet), the skin impedance was measured when 0, 30, and 60 minutes elapsed since the thin film sheet was peeled off (or immediately after lotion was sprayed in the case of not attaching the thin film sheet). For the measurement, a skin impedance measuring device "SKINCON-200EX" (manufactured by Yayoi Co., Ltd., skin surface stratum corneum water content measuring device) was used.

Figure 2:
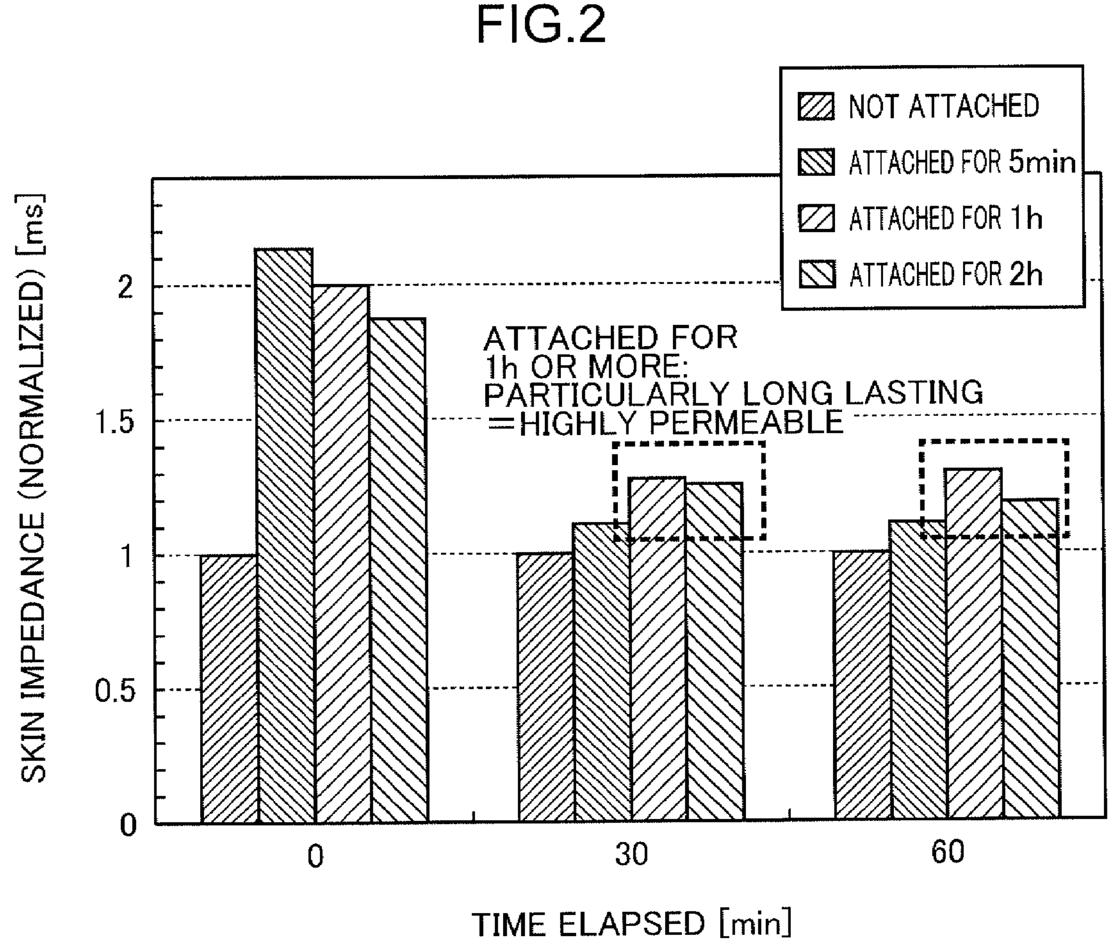
FIG. 2 is a graph illustrating the test results of Test Example 1 in Examples.

The results are illustrated in FIG. 2. As is clear from the graph in FIG. 2, it can be seen that higher moisturizing properties are achieved in the case of using the thin film sheet of the present invention than in the case of applying lotion directly to the skin. In particular, in a case where the thin film sheet was attached for 1 hour or more, the high moisturizing effect lasted when 60 minutes elapsed since the thin film sheet was peeled off.

Hence, it was confirmed that high moisturizing properties and its lasting effect are acquired by using the laminate sheet of the present invention.

Test Example 2: Confirmation of Local Moisturizing Effect

Figure 3:
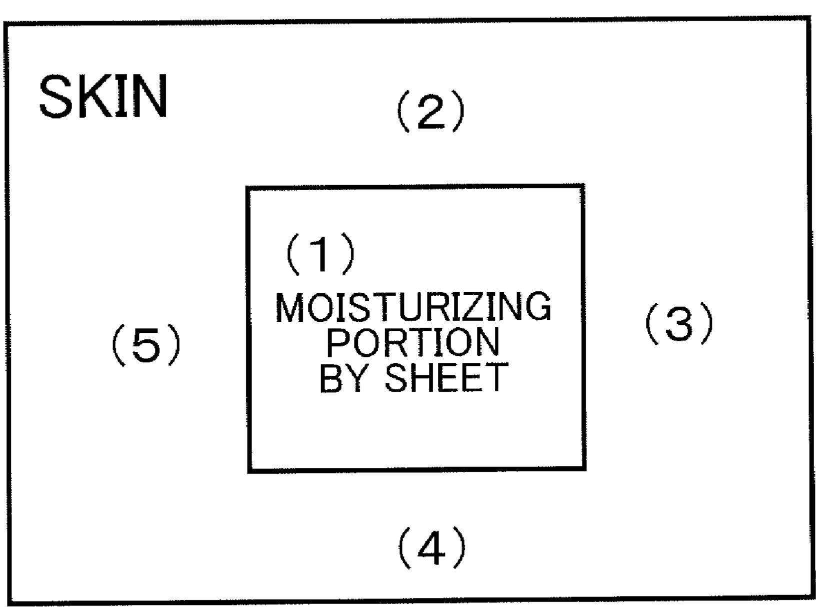
FIG. 3 is a schematic view illustrating a place where skin impedance is measured in a test conducted in Test Example 2 in Examples.

The laminate sheet obtained above was attached to the skin of a subject, and an equal amount of commercially available moisturizing lotion was sprayed on the moisturizing portion by sheet (1) and the peripheral portions of sheet attached portion (2) to (5) illustrated in FIG. 3. Immediately after that, the support of the laminate sheet was peeled off, and the thin film sheet was left attached as it was for 1 hour. When 1 hour elapsed, the thin film sheet was peeled off.

Then, at the time point at which 1 hour elapsed since the sheet was peeled off, the skin impedance at the moisturizing portion by sheet (1) and the peripheral portions of sheet attached portion (2) to (5) were measured using the same measuring device as in Test Example 1.

The results are presented in Table 1.

TABLE 1

| | Skin impedance 1 hour after peeling off (mS) | Determination of moisturization |
|---|---|---|
| Sheet attached portion (1) | 77 | Good |
| Peripheral portion of attached portion (2) | 54 | Poor |
| Peripheral portion of attached portion (3) | 51 | Poor |
| Peripheral portion of attached portion (4) | 53 | Poor |
| Peripheral portion of attached portion (5) | 61 | Poor |

From the results in Table 1, it was found that the moisturizing effect lasted even when 1 hour elapsed since the sheet was peeled off at the place to which the sheet of the present invention was attached. On the other hand, at the peripheral portions of sheet attached portion, only the same degree of moisturizing effect as in the case of not spraying moisturizing lotion was acquired. From the above, it was confirmed that it is possible to allow the cosmetic ingredients to permeate the places where the cosmetic effects are locally desired by using the laminate sheet of the present invention.

This application is based on Japanese Patent Application No. 2020-210120 filed on Dec. 18, 2020, the contents of which are included in the present application.

In order to express the present invention, the present invention is described above appropriately and sufficiently through the embodiments with reference to specific examples, drawings and the like. However, it should be recognized by those skilled in the art that changes and/or improvements of the above-described embodiments can be readily made. Accordingly, changes or improvements made by those skilled in the art shall be construed as being included in the scope of the claims unless otherwise the changes or improvements are at the level which departs from the scope of the appended claims.

INDUSTRIAL APPLICABILITY

The present invention has a wide range of industrial applicability in the technical field relating to cosmetics and beauty.

The invention claimed is:

1. A cosmetic laminate sheet comprising:

a thin film sheet that has a thickness of 10 nm or more and 10 μm or less and is water-permeable; and a support that is laminated on the thin film sheet and has water absorbing properties, wherein, as a water capacity, the support is configured to contain 4.4 g or more of water per 1 g of the support, wherein the thin film sheet has pores having a diameter of 10 nm or more and 100 μm or less, wherein the pores are defined by through-holes, and wherein a porosity of the thin film sheet is in a range of 1% or more and 10% or less in area ratio.

2. The cosmetic laminate sheet according to claim 1, wherein the water capacity is 10 $mg/cm^2$ or more and 17 $mg/cm^2$ or less.

3. The cosmetic laminate sheet according to claim 1, wherein the thin film sheet is hydrophilic.

4. A method for attaching the thin film sheet of the cosmetic laminate sheet according to claim 1 to an adherend, the method comprising:

placing the cosmetic laminate sheet on the adherend such that the thin film sheet is in contact with the adherend, spraying cosmetic ingredients over an entirety of the support from a support side, and peeling the support off from the thin film sheet.

5. The method according to claim 4, wherein the cosmetic ingredients constitute a liquid.

6. The method according to claim 5, wherein the liquid is a lotion, milky lotion, or whitening ingredients.

7. A method for attaching the thin film sheet of the cosmetic laminate sheet according to claim 1 to an adherend, the method comprising:

immersing the cosmetic laminate sheet in cosmetic ingredients, placing the cosmetic laminate sheet on the adherend such that the thin film sheet is in contact with the adherend, and peeling the support off from the thin film sheet.

8. The method according to claim 7, wherein the cosmetic ingredients constitute a liquid.

9. The method according to claim 8, wherein the liquid is a lotion, milky lotion, or whitening ingredients.

* * * * *